United States Patent [19]

Botta et al.

[11] Patent Number: 5,723,694
[45] Date of Patent: Mar. 3, 1998

[54] PROCESS FOR PREPARING MONOMETHYLATED OR DIMETHYLATED PHENOLS

[75] Inventors: Artur Botta; Hans-Josef Buysch, both of Krefeld, Germany

[73] Assignee: Bayer Aktiengesellschaft, Leverkusen, Germany

[21] Appl. No.: 755,513

[22] Filed: Nov. 22, 1996

[30] Foreign Application Priority Data

Dec. 4, 1995 [DE] Germany .................. 195 45 105.8

[51] Int. Cl.$^6$ .................................................. C07C 37/00
[52] U.S. Cl. ..................... 568/799; 568/607; 568/609; 568/659; 568/660; 568/662; 568/626
[58] Field of Search ....................... 568/607, 609, 568/659, 660, 662, 626, 799

[56] References Cited

U.S. PATENT DOCUMENTS

| | | |
|---|---|---|
| 4,475,001 | 10/1984 | Leston . |
| 4,480,140 | 10/1984 | Leston . |
| 4,538,009 | 8/1985 | Goetz et al. ..................... 568/799 |
| 4,769,501 | 9/1988 | Iwahara et al. .................. 568/799 |

OTHER PUBLICATIONS

K–D. Bode, V. Herstellung von Phenolen bzw. Phenol–Derivaten aus anderen Phenolen unter Erhaltung der phenolischen Funktion, Methoden der Organischen Chemie (Houben–Weyl), Band VI/1c, p. 925, (1976).
B. Delmon, et al., Zeolites as Catalysts, Sorbents and Detergent Builders Applications and Innovations, Studies in Surface Science and Catalysis, vol. 46, pp. 168–179, (1989).
H. Fiege, Ullmann's Encyclopedia of Industrial Chemistry, Fifth, Completely Revised Edition, Cresols and Xylenols, vol. A 8, p. 25 (1975).

*Primary Examiner*—Paul F. Shaver
*Attorney, Agent, or Firm*—Sprung Kramer Schaefer & Briscoe

[57] ABSTRACT

Phenols monomethylated or dimethylated in the ortho or para position to the OH group and having the formula

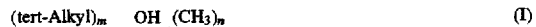
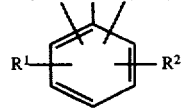

can be prepared by reaction of tert-alkyl-substituted phenols of the formula

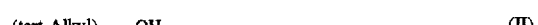
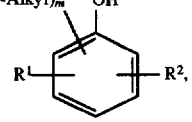

in which at least one free ortho or para position to the OH group is present, in three reaction steps a), b) and c). In a), (II) is reacted with formaldehyde or its polymers and a carboxylic acid of the formula $$R^3\text{—COOH},\qquad\text{(III)}$$

which gives a mixture of substituted phenols of the formulae

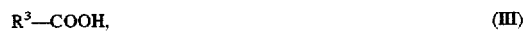
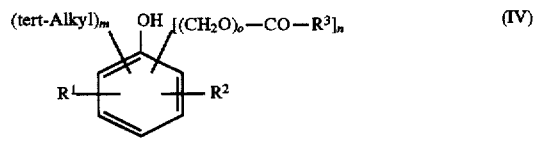

and

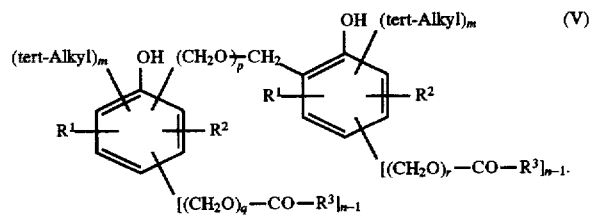

In b) the mixture of (IV)/(V) is hydrogenated using catalytically activated hydrogen to give the substituted phenols of the formula

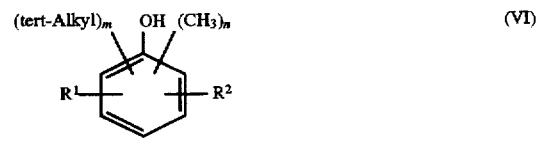

which, if m=0, are reacted in c) in the presence of an acid cleavage catalyst with elimination of tert-alkenes to give the methylated phenols of the formula (I).

Before or during the hydrogenation, the phenols of the formulae (IV) and (V) can be reacted with the aid of an alcohol of the formula $$R^4\text{—OH}\qquad\text{(VII)}$$

to give a mixture of the etherified substituted phenols of the formulae

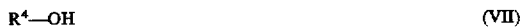
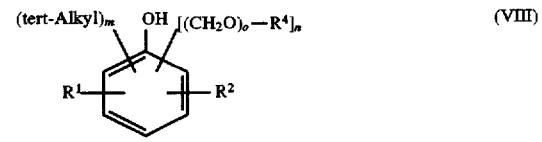

and

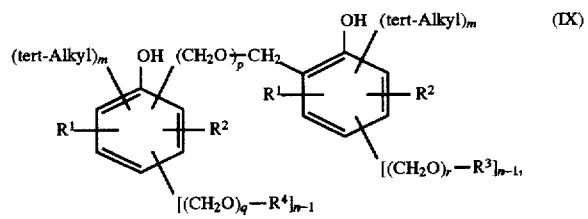

which can then, in the manner indicated, be hydrogenated and freed of the tert-alkyl groups.

12 Claims, No Drawings

PROCESS FOR PREPARING MONOMETHYLATED OR DIMETHYLATED PHENOLS

BACKGROUND OF THE INVENTION

1. Field of the Invention

The invention relates to a process for preparing phenols which are monomethylated or dimethylated in the ortho or para position to the OH group, with the ortho and para positions not to be methylated being protected by tert-alkyl groups. The methylation is carried out by first carrying out a reaction with formaldehyde or its polymers and a carboxylic acid in the free ortho or para positions, with one or more molecules of formaldehyde being attached to the positions to be methylated and being capped by 1 mol of a carboxyl group to form an alkylcarbonyloxy group. This group formed from formaldehyde and carboxylic acid is catalytically hydrogenated to form a methyl group. Before or during the hydrogenation, the terminal alkylcarbonyloxy group can be removed by means of an alcohol and converted into a terminal ether group. Furthermore, it has been observed that the methylol group produced by reaction with formaldehyde can, instead of being capped by the carboxylic acid, can also react with the methylol group of another molecule of the phenol to be reacted to form ether bridges. The reaction with formaldehyde and carboxylic acid can advantageously be carried out in the presence of a basic catalyst.

2. Description of the Related Art

Numerous methods for the methylation of phenol to give cresols and xylenols are known. Industrial use is made, for example, of the gas-phase methylation of phenol with methanol to give ortho-cresol or ortho-,ortho'-dimethylphenol which is, for example, an intermediate for polyphenylene oxide (PPO) (Houben-Weyl, Methoden der organischen Chemie, 4th edition, Volume VI/lc, (1976), 925–1059; Ullmann's Encyclopedia of Industrial Chemistry, Vol. A8, 15–59 (1987)). For this reaction, a series of very effective ortho-directing catalysts is known (MgO at a reaction temperature of 460° C.; $MnO_2$ at 420° C.; $Cr_2O_3$ at 390° C.; $\gamma$-$Al_2O_3$ at 360° C.; iron oxides containing Si, Mg, Cr, Mn, Sn, Zn, Ge, V at 350° C.). However, disadvantages are the high reaction temperatures required and the sometimes low mechanical stability of the catalysts. A further deficiency, particularly in the case of the iron oxide cataylsts, is that the alkylating agent methanol has to be used in a 6- to 10-fold excess, since during the reaction it is decomposed mainly into a mixture of $H_2$, $CH_4$ and CO; to this is added the formation of dimethyl ether observed under such conditions.

Although there is an extremely wide variety of literature references on the subject of the gas-phase methylation of phenol in the ortho positions, there are only few and frequently not very reliable literature sources for methylations in the meta or para position, these mentioning zeolites of the Y type, $H_3PO_4$ on kieselguhr or boric acid on $SiO_2$ as catalysts (R. F. Parton et al., Proceedings of an International Symposium, Würzburg, 4–8 Sep. 1988, published in Studies in Surface Science and Catalysis, Volume 46 (1989), 168–178, Elsevier Science Publishers B. V., Amsterdam).

In the case of a targeted monomethylation of substituted phenols, there is the additional difficulty of a plurality of competing substitution positions, so that it is difficult to realize the desired, but possibly not favored, substitution; for example in the reaction of meta-cresol, methylating the sterically shielded 2 position instead of the favored 6 position. A preparation of 2,3-dimethylphenol which this would make possible is of industrial interest since this phenol is a basic building block for vitamin E.

There have already been proposals for blocking preferred substitution positions prior to the methylation by means of protective groups which can later be cleaved off again. For example, phenols having a plurality of substitutable positions are, according to U.S. Pat. No. 4,480,140, partially protected by prior halogenation with chlorine or bromine and, according to U.S. Pat. No. 4,475,001, by tert-butylation with isobutene. Of these two methods, cleaving-off the halogen again from aromatics by hydrogenation does present a technical problem. According to both the US Patents mentioned, the alkylation is then carried out via the aminomethylation of the protected phenols using an aldehyde and a secondary amine, whereupon the Mannich base thus formed is reduced by splitting off the secondary amine by hydrogenation in the presence of a metal catalyst to form the alkyl group determined by the aldehyde. However, as can be seen from the comparative examples described further below, the hydrogenation of the dialkylaminomethyl group does not proceed sufficiently selectively to form the alkyl group, but a reductive elimination of the entire dialkylaminoalkyl group from the aromatic ring occurs to a considerable degree, so that reformation of the starting phenol takes place. This represents a significant deficiency in respect of the economics of the process.

SUMMARY OF THE INVENTION

A process has now been found for preparing phenols monomethylated or dimethylated in the ortho or para position to the OH group and having the formula

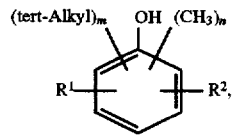

(I)

where

R[1] and R[2] represent, independently of one another, hydrogen, $C_1$–$C_{12}$-alkyl without tert-alkyl groups, $C_5$–$C_8$-cycloalkyl, phenyl, $C_1$–$C_4$-alkyl-phenyl, $C_7$–$C_{10}$-aralkyl, phenoxy, phenylthio or together represent a condensed aromatic ring, m is 0, 1 or 2 and if m=1 or 2 simultaneously indicates an ortho or para position to the OH group and n is 1 or 2 and at the same time indicates one or two of the ortho or para positions to the OH group, which comprises reacting tert-alkyl-substituted phenols having at least one free ortho or para position to the OH group and having the formula

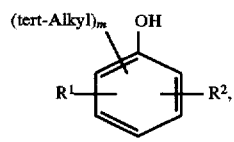

(II)

where

R[1] and R[2] are as defined above, tert-Alkyl has from 4 to 6 carbon atoms and m is as defined above and there are n free ortho or para positions to the OH group.

a) with from 1 to 20 mol of formaldehyde or its polymers and with at least 1 mol of a carboxylic acid of the formula $$R^3—COOH, \quad (III)$$

where

R³ is H, $C_1$–$C_{18}$-alkyl, $C_2$–$C_{18}$-alkenyl, $C_5$–$C_8$-cycloalkyl, $C_7$–$C_{10}$-aralkyl, phenyl or $C_1$–$C_4$-alkylphenyl, in the presence or absence of an inert solvent to give a mixture of substituted phenols of the formulae

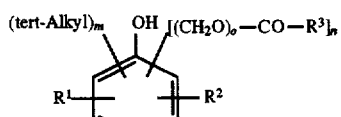   (IV)

and

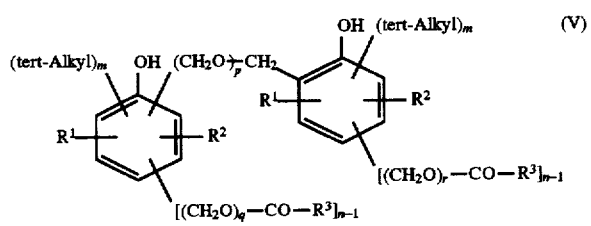   (V)

where

R¹, R², R³, tert-Alkyl, m and n are as defined above and o, p, q and r are, independently of one another, from 1 to 8.

b) hydrogenating the compounds (IV) and (V) individually or as a mixture using $H_2$ in the presence of a hydrogenation catalyst to give substituted phenols of the formula

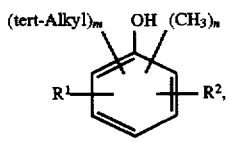   (VI)

where R¹, R², tert-Alkyl, m and n are as defined above, where the hydrogenation is carried out in the presence or absence of a solvent and where the substituted phenols of the formulae (IV) and (V) can be reacted individually or as a mixture, prior to or during the hydrogenation, with an alcohol of the formula $$R^4—OH, \quad (VII)$$

where

R⁴ represents $C_1$–$C_{18}$-alkyl, $C_2$–$C_6$-hydroxyalkyl or $C_5$–$C_8$-cycloalkyl, to give etherified, substituted phenols of the formulae

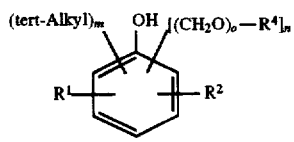   (VIII)

or

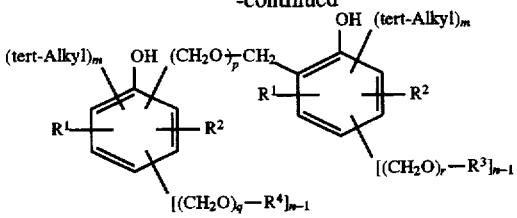   (IX)

where

R¹, R², tert-Alkyl, m, n, o, p, q and r are as defined above and c) if m is 0, the tert-alkyl groups are cleaved off at from 80° to 300° C. in the presence of an acid cleavage catalyst.

DETAILED DESCRIPTION OF THE INVENTION

The process of the invention can be represented by the reaction scheme 1 below:

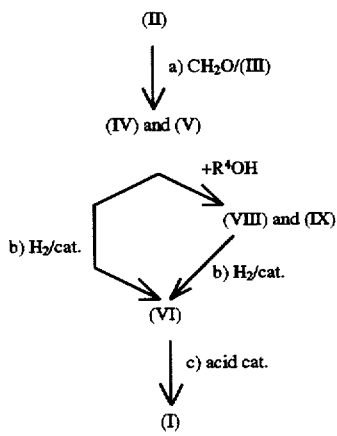

Furthermore, the process of the invention can be illustrated by the reaction schemes 2 and 3 for selected examples in which meta-cresol is first selectively protected by two or one tert-butyl protective groups, after which acetoxymethyl groups are introduced using formaldehyde and acetic acid in the presence of an amine catalyst at 100° C. and are then hydrogenated at 120° C. by means of hydrogen in the presence of a Pd catalyst to give a methyl group. Subsequently, the tert-butyl groups are cleaved off as i-butylene at 200° C. in the presence of sulfuric acid. With regard to the above indices o, q and r, it is possible, to a lesser degree, that the methylol group first formed from 1 mol of formaldehyde is not immediately reacted with acetic acid in the sense of an esterification, but firstly one or more mol of formaldehyde react with the first methylol group to form ether groups before the terminal OH groups formed are then also capped by esterification with acetic acid. Furthermore, as shown in formula (V), two methylol groups can also react with one another to form an ether group.

Reaction scheme 2:

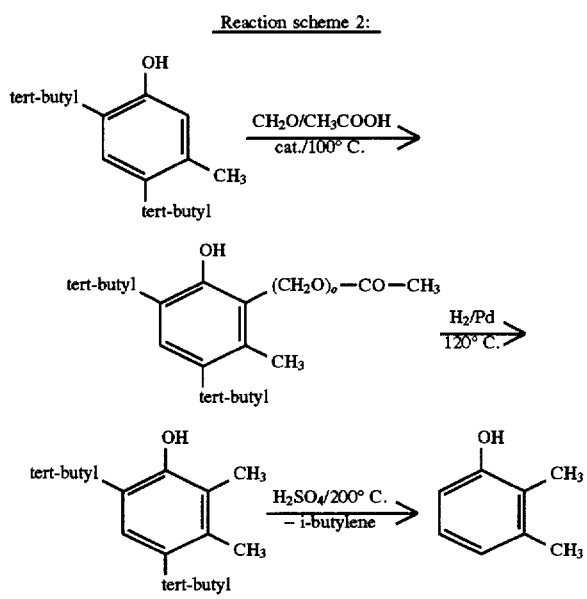

Reaction scheme 3:

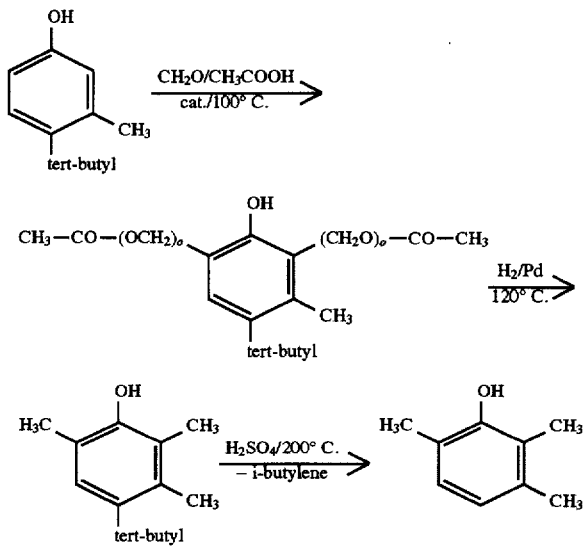

The phenols formed in the reaction schemes 2 and 3, namely 2,3-dimethylphenol and 2,3,6-trimethylphenol are precursors for the synthesis of vitamin E.

Compared with processes of the prior art, the process of the invention gives higher selectivities in the monomethylation or dimethylation and thus also higher purities which become apparent both in the reaction with formaldehyde or its polymers and carboxylic acid and also in the hydrogenation of the intermediates. These advantages are the result of the gentle reaction conditions employed according to the invention. The monomethylation or dimethylation occurs at one or two of the ortho or para positions to the OH group. Ortho or para positions which are not to be methylated are occupied by tert-alkyl groups. Such an occupation is not necessary to the extent that $R^1$ or $R^2$ are in such positions. It is thus possible, for example to exhaustively methylate p-cresol in the 2 and 6 positions to the OH group without use of tert-alkyl groups, to give 2,4,6-trimethylphenol. If tert-alkyl groups are present, these can be cleaved off in the last process step c) if such groups are not desired in the end product, i.e. m=0. However, it is likewise possible to leave the tert-alkyl groups in the end product where they may again act as blocking protective groups in further reactions of the end product.

$C_1$–$C_{12}$-alkyl or $C_1$–$C_{18}$-alkyl are, for example, methyl, ethyl, propyl, isopropyl, butyl, isobutyl, pentyl, hexyl, 2-ethyl-hexyl, octyl, decyl, dodecyl, palmityl or stearyl. For $C_1$–$C_{12}$-alkyl in the context of $R^1$ and $R^2$, the tert-alkyl groups are excepted.

$C_2$–$C_{18}$-alkenyl is the same as the corresponding alkyl except for the presence of a C=C double bond and is, for example, vinyl, allyl, butenyl, pentenyl, hexenyl, octenyl, decenyl, dodecenyl, hexadecenyl or octadecenyl.

$C_5$–$C_8$-cycloalkyl is, for example, cyclopentyl, methyl-cyclopentyl, dimethyl-cyclopentyl, cyclohexyl, methyl-cyclohexyl, dimethyl-cyclohexyl, cycloheptyl or cyclooctyl.

$C_7$–$C_{10}$-aralkyl is, for example, benzyl, α- or β-phenylethyl, phenylpropyl or phenylbutyl.

Phenyl can be substituted by $C_1$–$C_4$-alkyl, so that, for example, tolyl or ethylphenyl substituents result.

$R^1$ and $R^2$ can also together be a condensed aromatic ring; accordingly, the process of the invention can also be employed not only for phenols but also, for example, for naphthols.

tert-Alkyl has from 4 to 6 carbon atoms and accordingly represents tert-butyl, tert-amyl or tert-hexyl, where in the latter case the tertiary carbon atom forms the bond to the aromatic ring of the phenol.

$C_2$–$C_6$-hydroxyalkyl is, for example, 2-hydroxy-ethyl, 2-hydroxy-propyl, 3-hydroxy-propyl and the homologous substituents having up to 6 carbon atoms.

The index n assumes the numerical value 1 or 2 and at the same time indicates that the substituents to which the index n refers are located in the ortho or para position to the OH group. The starting phenol (II) has n free ortho or para positions to the OH group.

The index m is 0, 1 or 2; in the same way as the index n, m also indicates an ortho or para position. The sum of m and n is 3 in agreement with the number of ortho and para positions, but if $R^1$ and/or $R^2$ are located in ortho or para positions can also be 2 or 1.

The starting phenols of the formula (II) can be prepared as described in the two abovementioned US patents and are often industrially readily available intermediates or coupled-production products in other processes of phenol chemistry whose amount can, depending on utilization of capacity, fluctuate greatly on a temporary basis and in many cases constitute an undesired but unavoidable material. Thus, the process of the invention at the same time makes possible the conversion of such unavoidably obtained material into worthwhile and useful products, making the disposal of such unavoidably obtained material, which would be ecologically and economically troublesome, at least partly superfluous.

The starting phenols of the formula (II) have at least one free ortho or para position to the OH group. Examples are: 2-tert-butyl-3-methylphenol, 2-tert-butyl-4-methylphenol, 2-tert-butyl-5-methylphenol, 2-tert-butyl-6-methylphenol; the homologs of the specified 2-tert-butyl-alkylphenols in which the place of the methyl substituent is taken by ethyl, propyl,butyl, cyclohexyl, benzyl, phenyl or phenoxy as substituents. Other examples are 2-tert-butyl-3,5-, -3,6-, -4,5-, -5,6-dimethylphenol. Furthermore, the place of 2-tert-butyl can be taken by the 2-tert-pentyl group or the 2-terthexyl group. Further individual examples in a listing which is not exhaustive are: 2-tert-hexyl-4-(or -5-)methyl(or ethyl) -phenol, 4-tert-butyl-4-(or -5-)methyl(or ethyl)-phenol, 4-tert-butyl-2(or -3-)-isopropyl(or hexyl, cyclopentyl, phenyl or phenoxy)-phenol; 4-tert-pentyl-2,5-dimethylphenol, 4-tert-butyl-2,3-dimethylphenol, 4-tert-butyl-5-isopropyl-3-ethylphenol, 4,6-di-tert-butyl-3-(or -5-)methylphenol, 4,6-di-tert-butyl-3,5-dimethylphenol, 4,6-di-tert-pentyl-3-heptylphenol, 4,6-di-tert-butyl-3-cyclohexyl(or 3-phenyl, 3-phenylthio)-phenol; 2,6-di-tert-butyl-3(or -5)-methylphenol, 2,6-di-tert-pentyl-3-isopropyl(or-3-pentyl, -3-nonyl, 3-phenyl or 3-phenoxy)-phenol, 2-tert-butyl-1-naphthol, 2-tert-butyl-3-methyl- 1-naphthol, 4-tert-butyl-2-naphthol, 4-tert-butyl-3-isopropyl-1-naphthol or -2-naphthol.

Preferably, the place of $R^1$ and $R^2$ is taken by the radicals $R^{11}$ or $R^{12}$ which, independently of one another, represent hydrogen, $C_1$–$C_4$-alkyl apart from tert-butyl or benzyl or are together a condensed aromatic ring. Particularly preferably, the place of $R^{11}$ and $R^{12}$ is taken by the radicals $R^{21}$ and $R^{22}$ which, independently of one another, represent hydrogen, methyl or ethyl or are together a condensed aromatic ring.

Furthermore, it is preferred that the tert-alkyl radical has 4 carbon atoms and is accordingly tert-butyl.

Carboxylic acids of the formula (III) are, for example, formic acid, acetic acid, propionic acid, butyric acid, isobutyric acid, valeric acid, pivalic acid, isovaleric acid, caproic acid, enanthic acid, capric acid, caprylic acid, undecanoic acid, dodecanoic acid, palmitic acid, 2-ethyl-hexanoic acid, cyclohexane-carboxylic acid, acrylic acid, methacrylic acid, crotonic acid, undecenoic acid, oleic acid, phenylacetic acid, hydrocinnamic acid, cinnamic acid, benzoic acid, toluic acid. For reasons of ready availability and the absence of secondary reactions (e.g. complete or partial hydrogenation of unsaturated acids), the lower aliphatic carboxylic acids, in particular acetic acid, are preferred. The place of the radical $R^3$ is therefore preferably taken by the radical $R^{13}$ having the meaning $C_1$–$C_4$-alkyl.

In the process of the invention, at least 1 mol, for example from 1 to 20 mol, preferably from 1 to 15 mol, particularly preferably from 1 to 10 mol, of the carboxylic acid of the formula (III) is used per mol of tert-alkyl-substituted phenol of the formula (II). In any case, a molar excess of carboxylic acid is not critical. Therefore, it is also possible to use the lower examples of the carboxylic acids mentioned, which are in a liquid state, as solvent and reaction medium, so that their amount exceeds the molar amounts specified.

Formaldehyde is used in the process of the invention as such or as a polymer thereof, for example as paraformaldehyde. The amount used is from 1 to 20 mol, preferably from 1 to 15 mol, particularly preferably from 1 to 10 mol, per mol of tert-alkyl-substituted phenol of the formula (II).

The reaction step a) of the process of the invention can be carried out either in the presence or in the absence of an inert solvent. The presence of such a solvent is useful particularly when the reaction is to be carried out in the presence of a carboxylic acid (III) which is solid under the reaction conditions. Inert solvents suitable for this purpose are, for example, hydrocarbons such as hexane, cyclohexane, petroleum ether, ligroin, benzene, toluene, the 3 isomeric xylenes (also as a mixture), tetralin, decalin; ethers such as diethyl ether, di(iso)propyl ether, di(n-, iso- or sec-)butyl ether, diamyl ether, 1,2-dimethoxyethane (cellosolve), tetrahydrofuran, dioxane or anisole; alcohols such as those mentioned above, which are, however, preferably only used from reaction step b) onwards; amides such as dimethylformamide, diethylacetamide, N-methylpyrrolidone, N-methylcaprolactam and the like.

The amount of the inert solvent is from 0.5 to 20 times that of the phenol (II) used, preferably 1–10 times, particularly preferably 1–5 times that of the phenol.

To enable simpler work-up, the procedure without inert solvent is preferred, with, as already described above, excess lower carboxylic acid serving as reduction medium and solvent.

The reaction of the tert-alkyl-substituted phenols (II) with formaldehyde and carboxylic acid (III) proceeds in principle without additional catalyst. However, catalysts having a basic character can be used successfully in the process of the invention, for example salts of the carboxylic acid (III) used with alkali metal cations or alkaline earth metal cations, or bases such as hydroxides, carbonates or hydrogencarbonates of alkali metals or alkaline earth metals which form such salts with the carboxylic acids (III) used. Other catalysts having basic character which can be used are secondary or tertiary amines, for example amines containing 2 or 3 methyl, ethyl, propyl, isopropyl or butyl groups, also piperidine, N-methyl-piperidine, morpholine, piperazine, N,N'-dimethyl-piperazine, pyridine, dimethylamino-pyridine, imidazole, N-methylimidazole, diazabicyclononane, diazabicycloundecane, diazabicyclooctane (DABCO) or alkaline catalysts which are also known as transesterification catalysts, for example Sn or Ti salts of organic acids, e.g. dibutyltin oxide or dioctyltin oxide or tin dilaurate. The amount of catalyst used is 0.5–50 mol %, preferably 1–30 mol %, particularly preferably 5–20 mol %, based on (II).

In the reaction step a) of the process of the invention, 1 mol of the tert-alkyl-substituted phenol (II) per substitutable position (n=1 or 2) reacts with predominantly 1 mol of formaldehyde and with 1 mol of carboxylic acid (III). This gives a substituted phenol (IV) having the index o=1, i.e. in which one alkylcarbonyloxymethyl group is present per substitutable position. However, it is likewise possible for the methylol group which is introduced into the phenol (II) prior to the esterification with the carboxylic acid (III) to react first with a further molecule or with a plurality of further molecules of formaldehyde, before the ester-like capping by the carboxylic acid (III) occurs. Accordingly, the index o can also assume values of from 2 to 8, with the proportion of substituted phenols (IV) decreasing rapidly with such higher values for o. An analogous situation applies to the indices p, q and r in the substituted bisphenols (V) which result from reaction of the methylol groups of two molecules of substituted phenols with formation of an ether group.

The reaction temperatures in the reaction step a) are in the range from 50° to 200° C., preferably from 60° to 150° C., particularly preferably from 80° to 120° C.

The phenols obtained in the reaction step a) of the process of the invention, which are always a mixture of those of the formula (IV) and those of the formula (V) as well as species having various values of the indices o, p, q and r, are then, in the second reaction step b) of the process of the invention, reacted at the substitutable positions with catalytically activated hydrogen to form methyl groups from the abovementioned alkylcarbonyloxymethyl groups and ether groups. This reaction with catalytically activated hydrogen accordingly comprises an ester cleavage at the terminal $R^3$—CO—O group and also an ether cleavage of the bisphenol (V). Likewise, a hydrogenative ether cleavage represents the degradation of a plurality of formaldehyde molecules in the case where the indices o, p, q and r have values of 2 or more. It is therefore possible and sometimes desirable for the substituted phenols of the formulae (IV) and (V) in which the methylol groups are capped with carboxylic acid (III) to be converted by means of an alcohol of the formula (VII), before or during the hydrogenation in step b) of the process of the invention, from the esterified state into the etherified state of the formulae (VIII) and (IX). Such a conversion into the etherified state can be useful when the catalytic hydrogenation is carried out in a (pressure) reactor made of acid-sensitive material which could be damaged by acid (III) cleaved off during the hydrogenation. If the catalytic hydrogenation is carried out in an alcohol as reaction medium, such an etherification occurs at least partially simultaneously before the hydrogenative ether and ester cleavage commences.

Suitable alcohols (VII) for this process variant are, for example, the following: methanol, ethanol, propanol, isopropanol, butanol, isobutanol, pentanol, hexanol, 2-ethylhexanol, cyclohexanol, octanol, decanol, allyl alcohol, benzyl alcohol, phenylethyl alcohol, methoxypropanol, glycol, 1,2- and 1,3-propylene glycol, butylene glycol, preferably methanol and ethanol with $R^{14}$=methyl or ethyl. Alcohols of the type mentioned can at the same time serve as reaction medium for the hydrogenation in step b). If a complete conversion from the esterified state into the etherified state is desired, the amount of the alcohol (VII) to be used is at least 1 mol per substitutable position in the starting phenol. In general, larger amounts, for example from 1 to 10 mol of alcohol (VII) per substitutable position in the starting phenol, are employed. In the case of such an alcohol serving as reaction medium for the catalytic hydrogenation, its amount goes beyond this molar range and is from 100 to 2000% by weight of the mixture of (IV) and (V) or (VIII) and (IX) to be hydrogenated.

Hydrogenation catalysts for step b) of the process of the invention are all those with which those skilled in the art are familiar for this purpose. The hydrogenation-active component here is a noble metal from the platinum metal group, nickel, cobalt or copper/chromium. Such catalysts can be present on a support such as $SiO_2$, $Al_2O_3$, pumice, oxidic or salt-like supports; likewise it is also possible to use the metals as such, for example pulverulent noble metal such as platinum black or palladium powder; nickel can also be used, for example, as Raney nickel. Copper/chromium are generally used as oxidic catalysts, for example copper chromite. Particular preference is given to using palladium or platinum on carbon or Raney nickel.

The hydrogenation catalyst is used in an amount of from 0.1 to 50% by weight, preferably from 1 to 20% by weight, particularly preferably from 5 to 15% by weight, based on the total weight of the substituted phenols (IV) and (V) or (VIII) and (IX). The catalyst can be recovered and used a number of times. The hydrogenation can be carried out at atmospheric pressure, for example by simply passing hydrogen through the reaction mixture, or under increased pressure; the pressure range is accordingly from 1 to 150 bar, preferably from 20 to 120 bar.

The hydrogenation temperatures are in the range from 25° to 200° C., preferably from 50° to 180° C., particularly preferably from 80° to 150° C.

The methyl derivatives (VI) formed in the hydrogenation are isolated by mechanical separation from the catalyst, for example by pressure or by vacuum filtration or by centrifugation and subsequent taking off of the solvent, if desired under reduced pressure.

The reaction products of the reaction step a), namely those of the formulae (IV) and (V), can, in a preferred variant of the process of the invention, be hydrogenated directly and without intermediate isolation in the reaction step b) if a sufficient amount of the carboxylic acid (III), preferably a carboxylic acid having $R^3=C_1-C_3$-alkyl, preferably acetic acid, has been used as reaction medium. In this variant, the carboxylic acid (III) should be used in an amount, including its required molar ratio, of from 100 to 1000% by weight, based on starting phenol (II). However, the mixture of the substituted phenols (IV) and (V) can also be subjected to intermediate isolation by vacuum distillation of all volatile constituents and, for example, purified by recrystallization before it is passed to the hydrogenation in the reaction step b).

If inert solvents are used in addition to excess carboxylic acid (III) or excess alcohol (VII), those mentioned above, for example, are suitable.

The last reaction step c) of the process of the invention is the cleaving-off of the tert-alkyl groups serving as protective groups. Acid catalysts for this purpose are, for example: $H_2SO_4$, $H_3PO_4$, $P_2O_5$, $CH_3SO_3H$, $C_6H_5-SO_3H$ substituted by methyl or chlorine, $H_3BO_3$, heteropolyacids, superacids, activated aluminas or clays, Lewis acids such as $ZnCl_2$, $SnCl_4$, $TiCl_4$, $SbCl_5$, $AlCl_3$.

For the thermal, acid-catalyzed cleaving-off of the tert-alkyl groups, the substituted phenols (VI) can be used as such or after prior purification (distillation, vacuum distillation, recrystallization, etc.). The amount of acid catalyst of the abovementioned type is from 0.01 to 30% by weight, preferably from 0.1 to 10% by weight, particularly preferably from 0.5 to 5% by weight, based on the weight of the substituted phenols (VI). The reaction temperatures for this cleaving-off of the tert-alkyl groups are in the range from 80° to 300° C., preferably from 120° to 250° C., particularly preferably from 150° to 200° C. The cleaving-off of the tert-alkyl groups generally commences on heating the reaction mixture even before the above reaction temperatures are reached, as can be recognized, for example, from the escape of the corresponding iso-alkene, for example iso-butylene from a tert-butyl group, monitored via a bubble counter.

The selectively methylated phenols (I) can be isolated and purified by fractional distillation, if desired under reduced pressure, by recrystallization, by chromatographic methods or by a combination of a plurality of these.

The reaction steps a), b) and c) can, independently of one another, be carried out either batchwise or continuously. In the case of relatively small amounts, the batchwise procedure will be preferred. In the case of large production quantities, those working in chemical process engineering have available to them tube reactors or loop reactors in which the individual stages of the process of the invention can be carried out continuously, taking into consideration a sufficiently long reaction section. Thus, for example, the reaction step a) can be carried out in a loop or tube reactor, the reaction product taken off continuously can then be fed to the reaction step b), for example in the downflow mode in a hydrogenation reactor, and the reaction product taken off continuously there can be reacted in the reaction step c), for example in a cracking column.

EXAMPLES

Example 1

A solution of 441 g (2 mol) of 4,6-di-tert-butyl-3-methylphenol in 500 ml of toluene was allowed to run into a suspension of 120 g (4 mol) of paraformaldehyde in 1000 ml of acetic acid at 80° C. over a period of 1.5 hours and the mixture was stirred for a further 20 hours at 80° C. Subsequently, volatile components were taken off under reduced pressure. The residue was a yellowy crystalline mass (630 g) which had the following composition (GC):

| Proportion (%) | Compound |
| --- | --- |
| 1.2 | Starting material |
| 82.9 | Formula 1 with n = 1 |
| 8.9 | Formula 1 with n = 2 |
| 1.8 | Formula 1 with n = 3 |
| 0.9 | Formula 1 with n = 4 |
| 0.6 | Formula 1 with n = 5 |
| 0.2 | Formula 1 with n = 6 |
| 2.0 | Formula 2 |
| Remainder | Unknown compounds |

[Structures of Formula 1 and Formula 2 shown: Formula 1 is 4,6-di-tert-butyl-3-methylphenol with ortho substituent $-(CH_2O)_n-COCH_3$; Formula 2 is the bis-phenol ether with $-CH_2OCH_2-$ bridge.]

Example 2

The procedure of Example 1 was repeated, but at a reaction temperature of 100° C. The composition was:

| Proportion (%) | Compound |
| --- | --- |
| 0.1 | Starting material |
| 85.5 | Formula 1 with n = 1 |
| 2.5 | Formula 1 with n = 2 |
| 2.3 | Formula 1 with n = 3 |
| 1.5 | Formula 1 with n = 4 |
| 1.0 | Formula 1 with n = 5 |
| 0.8 | Formula 1 with n = 6 |
| 1.5 | Formula 2 |
| Remainder | Unknown compounds |

Recrystallization of the crude product from petroleum ether or acetone gives the compound of the formula 1 with n=1 as colorless crystals of M.p.: 119.5° C.

Example 3

88.24 g (0.4 mol) of 4,6-di-tert-butyl-3-methylphenol, 18.0 g (0.6 mol) of paraformaldehyde, 300 ml of acetic acid and 10 g of sodium acetate (anhydrous) were heated for 15 hours at 100° C. while stirring. After taking off the acetic acid under reduced pressure, the residue was taken up in 300 ml of toluene and shaken with 200 ml of $H_2O$ and the toluene phase was evaporated to dryness. The crystalline reaction mixture had the following composition:

| Proportion | Compound |
| --- | --- |
| 0.3 | Starting material |
| 93.2 | Formula 1 with n = 1 |
| 0.5 | Formula 1 with n = 2 |
| 0.6 | Formula 1 with n = 3 |
| 1.8 | Formula 1 with n = 4 |
| 0.4 | Formula 1 with n = 5 |
| 1.5 | Formula 2 |
| Remainder | Unknown compounds |

Example 4

A mixture of 110.3 g (0.5 mol) of 4,6-di-tert-butyl-3-methylphenol, 200 ml of acetic acid, 22.5 g (0.75 mol) of paraformaldehyde and 6.5 g (0.09 mol) of diethylamine was brought while stirring to 100° C. and was held for 5 hours at this temperature. After taking off volatile components under reduced pressure, this gave 153 g of a crystalline mass having the composition:

| Proportion (%) | Compound |
| --- | --- |
| 0.1 | Starting material |
| 87.7 | Formula 1 with n = 1 |
| 2.4 | Formula 1 with n = 2 |
| 0.3 | Formula 1 with n = 3 |
| 1.0 | Formula 1 with n = 4 |
| 5.8 | Formula 2 |
| Remainder | Unknown compounds |

Example 5

Using a method similar to Example 1, the reaction of 300 ml of propionic acid, 30 g (1 mol) of paraformaldehyde, 110.3 g (0.5 mol) of 4,6-di-tert-butyl-3-methylphenol and 150 ml of toluene gave, after stirring for 20 hours at 120° C., 165 g of a crystalline oil which solidified to give a crystalline mass and had the composition:

| Proportion (%) | Compound |
|---|---|
| 0.1 | Starting material |
| 75.0 | Formula 3 with n = 1 |
| 4.5 | Formula 3 with n = 2 |
| 3.2 | Formula 3 with n = 3 |
| 1.7 | Formula 3 with n = 4 |
| 0.5 | Formula 3 with n = 5 |
| 2.0 | Formula 2 |
| Remainder | Unknown compounds |

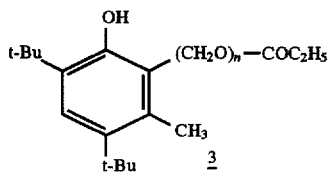

Example 6

Using the procedure of Example 1 to react 300 ml of pivalic acid, 30 g (1 mol) of paraformaldehyde, 110.3 g (0.5 mol) of 4,6-di-tert-butyl-3-methylphenol and 150 ml of toluene with another while stirring for 20 hours at 120° C. gave 175 g of a gradually crystallizing viscous oil having the composition:

| Proportion (%) | Compound |
|---|---|
| 0.1 | Starting material |
| 77.5 | Formula 4 with n = 1 |
| 5.6 | Formula 4 with n = 2 |
| 1.6 | Formula 4 with n = 3 |
| 1.9 | Formula 4 with n = 4 |
| 0.6 | Formula 4 with n = 5 |
| 0.5 | Formula 4 with n = 6 |
| 2.5 | Formula 2 |
| Remainder | Unknown compounds |

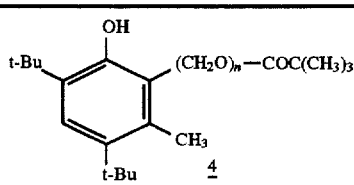

Example 7

The procedure of Example 1 was used to react 300 ml of acetic acid, 30 g (1 mol) of paraformaldehyde, 103.2 g (0.5 mol) of 2,4-di-tert-butyl-phenol and 150 ml of toluene with one another while stirring for 20 hours at 90° C. This gave 145 g of a yellowish oil which solidified after prolonged standing to give a crystalline mass. The composition of the mixture was as follows:

Example 8

63 g (about 0.2 mol) of the crude product as described in Example 1 were heated for 15 hours under reflux with 300 ml of methanol. After evaporating to dryness, the residue was distilled in an oil pump vacuum and recrystallized from ligroin. This gave colorless crystals of m.p.: 70° C. and b.p.$_{0.5}$: 115°–117° C. The yield was 39.5 g (75% of the theoretical yield) of 2-methoxymethyl-4,6-di-tert-butyl-3-methylphenol.

Example 9

63 g (about 0.2 mol) of the crude product as described in Example 1 were heated in an autoclave for 15 hours at 125° C. with 300 ml of ethanol. After cooling, excess ethanol and further volatile components were taken off under reduced

| Proportion (%) | Compound |
|---|---|
| 0.1 | Starting material |
| 78.9 | Formula 5 with n = 1 |
| 10.0 | Formula 5 with n = 2 |
| 2.5 | Formula 5 with n = 3 |
| 1.0 | Formula 5 with n = 4 |
| 1.0 | Formula 5 with n = 5 |
| 1.5 | Formula 6 |
| Remainder | Unknown compounds |

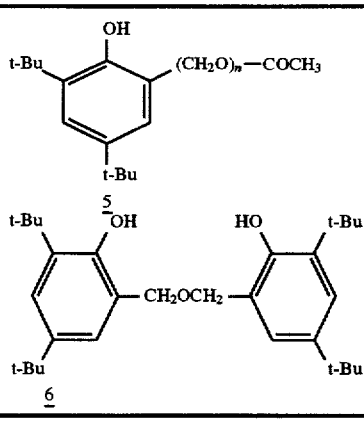

pressure. The remaining residue, which solidified to form a partially crystalline mass, contained 90.5% of 4,6-di-tert-butyl-2-ethoxymethyl-3-methylphenol according to GC-MS.

Comparative Examples 1 to 6

Various Mannich bases of the formula 7 were, on a scale of 0.5 mol of each, hydrogenated in a 2 l autoclave in 1000 ml of methanol as solvent at 20 bar of $H_2$ pressure. The reaction conditions, conversions and selectivities are shown in the table below; the reaction can be represented by the following reaction equation:

Examples 10 to 15

The 2-hydroxymethyl-phenols of the formula 10 which were esterified or etherified on the oxygen were hydrogenated. The reaction yields, conversions and selectivity are shown in the table below. The hydrogenation can be represented by the following equation:

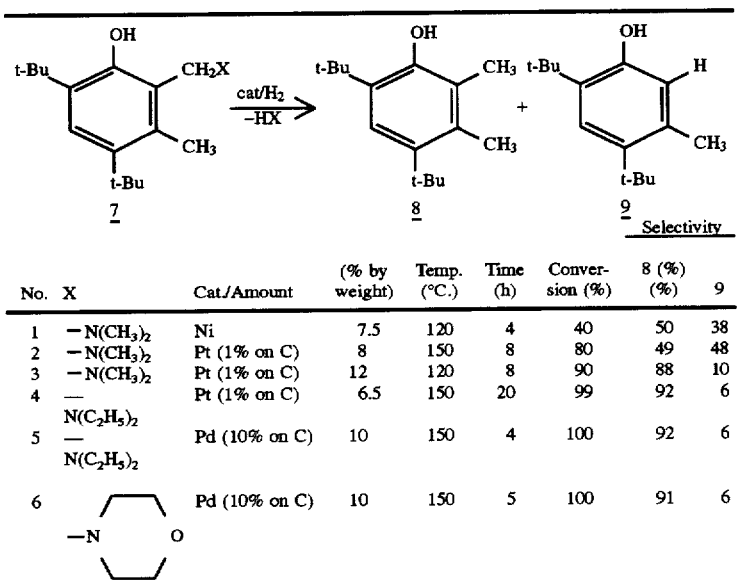

| No. | X | Cat./Amount | (% by weight) | Temp. (°C.) | Time (h) | Conversion (%) | 8 (%) Selectivity | 9 |
|---|---|---|---|---|---|---|---|---|
| 1 | —N(CH₃)₂ | Ni | 7.5 | 120 | 4 | 40 | 50 | 38 |
| 2 | —N(CH₃)₂ | Pt (1% on C) | 8 | 150 | 8 | 80 | 49 | 48 |
| 3 | —N(CH₃)₂ | Pt (1% on C) | 12 | 120 | 8 | 90 | 88 | 10 |
| 4 | —N(C₂H₅)₂ | Pt (1% on C) | 6.5 | 150 | 20 | 99 | 92 | 6 |
| 5 | —N(C₂H₅)₂ | Pd (10% on C) | 10 | 150 | 4 | 100 | 92 | 6 |
| 6 | —N⟨O⟩ | Pd (10% on C) | 10 | 150 | 5 | 100 | 91 | 6 |

| No. | Y | n | Cat./Menge | (% by weight) | Solvent | Parts by Volume |
|---|---|---|---|---|---|---|
| 10 | —COCH₃ | 1 | Pd (10% on C) | 11 | CH₃OH | 10 |
| 11 | —COCH₃ | 1–6 | Pd (10% on C) | 7 | CH₃OH | 3 |
| 12 | —COCH₃ | 1 | Pd (10% on C) | 5 | CH₃COOH | 3.5 |
| 13 | —COCH₃ | 1 | Raney Ni | 10 | CH₃COOH | 4 |
| 14 | —CH₃ | 1 | Pd (10% on C) | 12 | CH₃OH | 10 |

-continued $$\underset{10}{\underset{\text{t-Bu}}{\text{t-Bu}}\text{-}\underset{\text{CH}_3}{\text{C}_6\text{H}_2(\text{OH})(\text{CH}_2\text{O})_n\text{-Y}}} \xrightarrow{\text{cat/H}_2} \underset{8}{\underset{\text{t-Bu}}{\text{t-Bu}}\text{-}\underset{\text{CH}_3}{\text{C}_6\text{H}_2(\text{OH})(\text{CH}_3)}}$$

15  HO—t-Bu  1  Pd (10% on C)  10  CH₃COOH  15

—CH₂—C₆H₂(OH)(t-Bu)(CH₃)—

H₃C  t-Bu

| No. | H₂ (bar) | Temp. (°C.) | Time (h) | Conversion (%) | Selectivity 8 (%) |
|---|---|---|---|---|---|
| 10 | 20  | 150 | 4 | 100 | 97 |
| 11 | 20  | 150 | 4 | 100 | 99 |
| 12 | 20  | 120 | 6 | 100 | 98.9 |
| 13 | 100 | 120 | 5 | 100 | 98 |
| 14 | 20  | 150 | 4 | 100 | 95 |
| 15 | 100 | 120 | 5 | 100 | 99.5 |

Examples 16 to 19

In a 2 l Hastelloy autoclave (HC 4) fitted with propeller stirrer, the amounts shown in the table below of 4,6-di-tert-butyl-m-cresol, paraformaldehyde, acetic acid and diethylamine were made inert with nitrogen, heated to the temperature indicated and maintained at this temperature for the time indicated. The table shows the conversion determined by means of GC and the selectivity to 2-acetoxymethyl-4,6-di-tert-butyl-m-cresol (formula 1). The mixture obtained from this reaction was then admixed with the indicated amount of Pd catalyst (10% on activated carbon) and hydrogenated under the indicated conditions in respect of H₂, time and temperature. The table also gives the conversion and the selectivity to 4,6-di-tert-butyl-2,3-dimethylphenol (formula 8), calculated over both reaction stages.

| No. | Starting material (Mol) | CH₂O (Mol) | CH₃COOH (g) | Amine (Mol) | Temp. (°C.) | Time (h) | Conversion (%) | Selectivity (%) |
|---|---|---|---|---|---|---|---|---|
| 16 | 1   | 1.5  | 720 | —    | 100 | 8 | 99.5 | 95 |
| 17 | 1   | 1.5  | 650 | 0.15 | 100 | 5 | 99.5 | 96.5 |
| 18 | 1   | 1.5  | 650 | 0.35 | 100 | 4 | 99.2 | 96 |
| 19 | 1.5 | 2.25 | 720 | 0.25 | 120 | 4 | 99.7 | 96.5 |

| No. | Cat. (g) | H₂ (bar) | Temp. (°C.) | Time (h) | Conversion (%) | Selectivity of both stages (%) |
|---|---|---|---|---|---|---|
| 16 | 15   | 20  | 120 | 6   | 100  | 91 |
| 17 | 15   | 150 | 100 | 5   | 99.5 | 92 |
| 18 | 15   | 150 | 120 | 3   | 99.8 | 94.5 |
| 19 | 22.5 | 100 | 120 | 4.5 | 100  | 93.5 |

The reaction mixture from Example 19 was separated from the catalyst by filtration with suction and washing with acetic acid and worked up by distillation, first under atmospheric pressure, then under reduced pressure. The first fractions containing the solvent and the amine catalyst can be reused for repeat batches. The main fraction boiled at from 100° to 130° C. under 0.3 mbar. The yield of 4,6-di-tert-butyl-2,3-dimethylphenol was 314.5 g (89.5% of the theoretical yield). Recrystallization from petroleum ether gave colorless crystals of m.p.: 90°–93° C.

Examples 20 to 28

For the debutylation, 50 g in each case of 4,6-di-tert-butyl-2,3-dimethylphenol were admixed with the catalyst indicated in the table below in a 100 ml glass flask fitted with internal thermometer, magnetic stirrer, reflux condenser, gas cap, bubble counter and cold trap with dry ice cooling and were heated while stirring. The elimination of isobutene occurs in the temperature range from 130° to 180° C. and can be monitored at the bubble counter and by means of the condensation in the cold trap. The reaction mixture was maintained under reflux conditions until the elimination of isobutene was complete or ceased. The composition of the reaction mixture was determined by gas chromatography; this gave the amounts indicated in the table, with the remainder to 100% being unknown substances.

| No. | Cat. | Amount (Gew. %) | Temp. (°C.) | Time (h) | Selectivity of formula | | | |
|---|---|---|---|---|---|---|---|---|
| | | | | | 8 | 11 | 12 | 13 |
| 20 | $H_2SO_4$ conc. | 0.5 | 220 | 1 | 0.2 | 6.5 | 2.1 | 86 |
| 21 | $H_2SO_4$ conc. | 1 | 200–220 | 0.5 | 0.1 | 6.0 | 0.65 | 87.5 |
| 22 | $H_2SO_4$ conc. | 0.7 | 180–210 | 0.75 | — | 4.0 | 2.1 | 87 |
| 23 | $H_2SO_4$ conc. | 1.5 | 210–220 | 1.5 | 0.1 | 2.5 | 0.5 | 92.9 |
| 24 | $Al_2O_3$ | 20 | 240–250 | 1.75 | 41 | 20.0 | 3.9 | 28 |
| 25 | $Al_2O_3$ | 40 | 240–260 | 1.5 | 42 | 14.5 | 1.8 | 35 |
| 26 | $H_3PO_4$ (98%) | 4 | 220 | 1 | — | 2.5 | 4.5 | 86 |
| 27 | $CH_3SO_3H$ | 4 | 220 | 1 | — | 16.0 | 2.5 | 76 |
| 28 | p-$CH_3$—$C_6H_4$—$SO_3H$ | 6 | 210 | 1 | 0.9 | 5.5 | 10.5 | 77 |

Compounds

Formula 8 as above

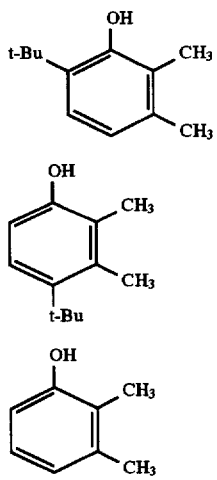

Example 29

In a 250 ml three-neck flask fitted with magnetic stirrer, $N_2$ inlet tube, internal thermometer, 10 cm Vigreux column, short-path distillation attachment, bubble counter and cold trap (dry ice), 0.75 g of conc. $H_2SO_4$ were added in portions by means of a dropping pipette to 100 g (0.43 mol) of 4,6-di-tert-butyl-2,3-dimethylphenol while passing in $N_2$ and heating and the mixture was then maintained at 250° C. for 3 hours while stirring. The elimination of isobutene commenced at about 140° C., and the 2,3-dimethylphenol distilled over at from 205° to 210° C. as an oil which solidified to a crystalline mass and had a purity of 97%. The conversion was 100%, the yield was 49 g (94% of the theoretical yield).

Example 30

Using a procedure similar to that of Example 4, 75.1 g (0.5 mol) of 2-tert-butylphenol, 40.0 g (1.33 mol) of paraformaldehyde, 300 ml of acetic acid and 9 g (0.12 mol) of diethylamine were reacted with one another while stirring for 6 hours at 100° C. to give a quantitative conversion of the starting phenol. The reaction mixture was subsequently hydrogenated for 6 hours at 120° C. and 100 bar of $H_2$ with addition of 8 g of Pd (10% on C) and 600 ml of further acetic acid using a method similar to Examples 10 to 15. According to GC, the conversion was 100% and the selectivity to 6-tert-butyl-2,4-dimethylphenol was 83%, based on the 2-tert-butylphenol used.

Example 31

Use of 82.2 g (0.5 mol) of 2-tert-butyl-5-methylphenol in place of 2-tert-butyl-phenol in the procedure of Example 30 and hydrogenation under the same conditions gave 6-tert-butyl-2,3,4-trimethylphenol in a yield of 78%, based on the starting phenol.

Example 32

Using a procedure similar to Example 30, 21.6 g (0.15 mol) of 2-naphthol, 250 ml of acetic acid, 6.8 g (0.225 mol) of paraformaldehyde and 2 g (0.026 mol) of diethylamine were reacted with one another at 80° C. while stirring for 4 hours, after which conversion was complete. In the subsequent hydrogenation with addition of 4 g of Pd (10% on C) and 600 ml of acetic acid, the reaction mixture gave, after 6 hours at 120° C. and 100 bar of $H_2$, 70.5% of 1-methyl-2-naphthol, based on the starting naphthol.

What is claimed is:

1. A process for preparing a phenol which is monomethylated or dimethylated in the ortho or para position to the OH group and which has the formula

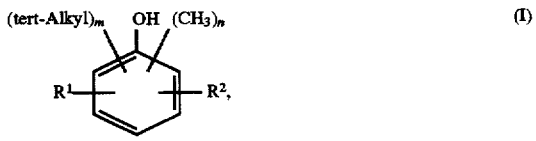

where $R^1$ and $R^2$ represent, independently of one another, hydrogen, $C_1$–$C_{12}$-alkyl without tert-alkyl groups, $C_5$–$C_8$-cycloalkyl, phenyl, $C_1$–$C_4$-alkyl-phenyl, $C_7$–$C_{10}$-aralkyl, phenoxy, phenylthio or together represent a condensed aromatic ring.

m is 0, 1 or 2 and if m=1 or 2 simultaneously indicates an ortho or para position to the OH group and n is 1 or 2 and at the same time indicates one or two of the ortho or para positions to the OH group, which comprises reacting a tert-alkyl-substituted phenol which has at least one free ortho or para position to the OH group and which has the formula

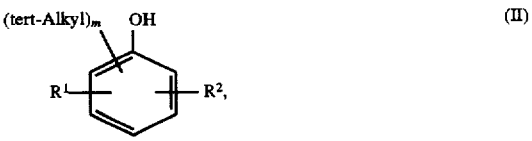

where $R^1$ and $R^2$ are as defined above, tert-alkyl has from 4 to 6 carbon atoms and m is as defined above and there are n free ortho or pars positions to the OH group, a) with from 1 to 20 mol of formaldehyde or its polymers and with at least 1 mol of a carboxylic acid of the formula

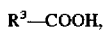

R³—COOH, (III)

where

R³ is H, $C_1$–$C_{18}$-alkyl, $C_2$–$C_{18}$-alkenyl, $C_5$–$C_8$-cycloalkyl, $C_7$–$C_{10}$-aralkyl, phenyl or $C_1$–$C_4$-alkyl-phenyl, in the presence or absence of an inert solvent to give a mixture of substituted phenols of the formulae

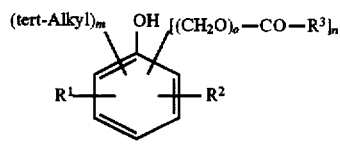

and

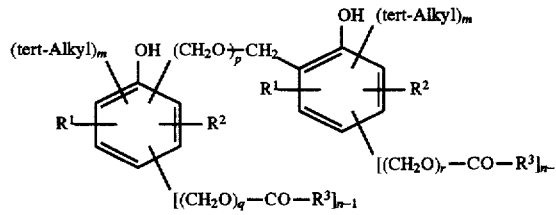

where $R^1$, $R^2$, $R^3$, tert-Alkyl, m and n are as defined above and o, p, q and r are, independently of one another, from 1 to 8, b) hydrogenating the compounds (IV) and (V) individually or as a mixture using $H_2$ in the presence of a hydrogenation catalyst to give a substituted phenol of the formula

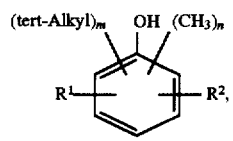

where $R^1$, $R^2$, tert-Alkyl, m and n are as defined above, where the hydrogenation is carried out in the presence or absence of a solvent and where the substituted phenols of the formulae (IV) and (V) can be reacted individually or as a mixture, prior to or during the hydrogenation, with an alcohol of the formula

R⁴—OH, (VII)

where

R⁴ represents $C_1$–$C_{18}$-alkyl, $C_2$–$C_6$-hydroxyalkyl or $C_5$–$C_8$-cycloalkyl, to give etherified, substituted phenols of the formulae

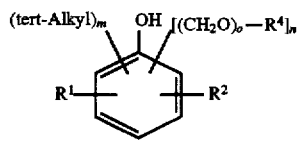

or

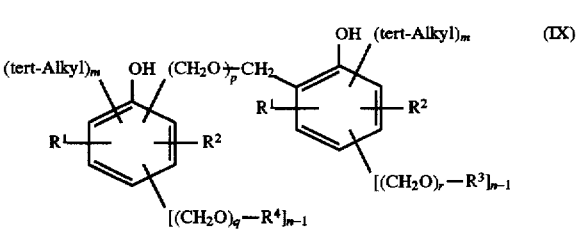

where $R^1$, $R^2$, tert-Alkyl, m, n, o, p, q and r are as defined above and c) if m is 0, the tert-alkyl groups are cleaved off at from 80° to 300° C. in the presence of an acid cleavage catalyst.

2. The process of claim 1, wherein the place of $R^1$ and $R^2$ is taken by the radicals $R^{11}$ and $R^{12}$ which, independently of one another, represent hydrogen, $C_1$–$C_4$-alkyl except for tert-butyl, phenyl or benzyl or are together a condensed aromatic ring.

3. The process of claim 2, wherein the place of $R^{11}$ and $R^{12}$ is taken by the radicals $R^{21}$ and $R^{22}$ which, independently of one another, represent H, $CH_3$ or $C_2H_5$ or are together a condensed aromatic ring.

4. The process of claim 1, wherein tert-alkyl is tert-butyl.

5. The process of claim 1, wherein from 1 to 15 mol of formaldehyde or its polymers are used.

6. The process of claim 5, wherein from 1 to 10 mol of formaldehyde or its polymers are used.

7. The process of claim 1, wherein from 1 to 15 mol of carboxylic acid $R^3$COOH are used.

8. The process of claim 7, wherein from 1 to 10 mol of carboxylic acid $R^3$COOH are used.

9. The process of claim 1, wherein the place of $R^3$ is taken by the radical $R^{13}$ which is $C_1$–$C_4$-alkyl.

10. The process of claim 9, wherein the place of $R^{13}$ is taken by the radical methyl.

11. The process of claim 1, wherein the reaction step a) is carried out in the presence of catalyst having basic character and selected from the group consisting of alkali metal or alkaline earth metal salts of carboxylic acids of the formula (III), secondary or tertiary amines and Sn and Ti salts of carboxylic acids (III).

12. The process of claim 1, wherein the place of $R^4$ is taken by the radical $R^{14}$ which is methyl or ethyl.

* * * * *

UNITED STATES PATENT AND TRADEMARK OFFICE
CERTIFICATE OF CORRECTION

PATENT NO. : 5,723,694
DATED : March 3, 1998
INVENTOR(S) : Botta, et al.

Page 1 of 2

It is certified that error appears in the above-identified patent and that said Letters Patent is hereby corrected as shown below:

Title Page  [57] ABSTRACT:: Line 31 delete formula (IX) and substitute

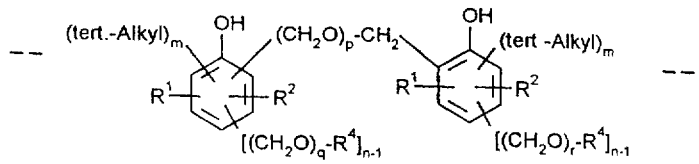

Col. 4, line 7    Delete formula (IX) and substitute

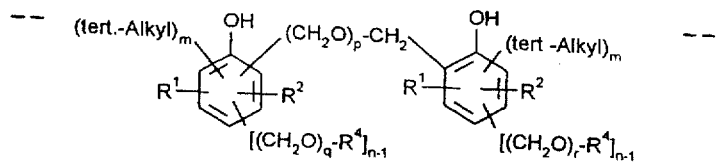

UNITED STATES PATENT AND TRADEMARK OFFICE
CERTIFICATE OF CORRECTION

PATENT NO.  : 5,723,694
DATED       : March 3, 1998
INVENTOR(S) : Botta, et al.

It is certified that error appears in the above-identified patent and that said Letters Patent is hereby corrected as shown below:

Col. 22, line 17    Delete formula (IX) and substitute

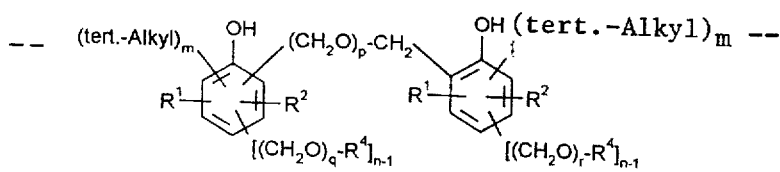

Signed and Sealed this

Twentieth Day of July, 1999

Attest:

Q. TODD DICKINSON

Attesting Officer    Acting Commissioner of Patents and Trademarks